(12) United States Patent
Sternby

(10) Patent No.: US 8,167,865 B2
(45) Date of Patent: May 1, 2012

(54) AVOIDING UNINTENTIONAL WITHDRAWAL OF ACCESS DEVICE FROM A VESSEL

(75) Inventor: Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 2219 days.

(21) Appl. No.: 10/471,626

(22) PCT Filed: Mar. 11, 2002

(86) PCT No.: PCT/SE02/00444
§ 371 (c)(1),
(2), (4) Date: Feb. 11, 2004

(87) PCT Pub. No.: WO02/072179
PCT Pub. Date: Sep. 19, 2002

(65) Prior Publication Data
US 2004/0116867 A1    Jun. 17, 2004

(30) Foreign Application Priority Data
Mar. 12, 2001 (SE) ....................... 0100838

(51) Int. Cl.
*A61M 31/00* (2006.01)
(52) U.S. Cl. ....................................... 604/500
(58) Field of Classification Search ............. 604/28, 604/39, 43, 44, 500–522, 164.09, 164.11, 604/191, 93.01, 94.01
See application file for complete search history.

(56) References Cited

U.S. PATENT DOCUMENTS

| 3,900,026 A | 8/1975 | Wagner ...................... 128/133 |
| 4,808,160 A * | 2/1989 | Timmons et al. .......... 604/94.01 |
| 4,822,341 A | 4/1989 | Colone ......................... 604/175 |
| 5,084,026 A | 1/1992 | Shapiro ........................ 604/179 |
| 5,112,313 A | 5/1992 | Sallee .......................... 604/180 |
| 5,171,216 A * | 12/1992 | Dasse et al. .................... 604/43 |
| 5,578,003 A | 11/1996 | Borger ........................... 604/65 |
| 6,090,048 A | 7/2000 | Hertz et al. .................... 600/485 |
| 6,506,182 B2 * | 1/2003 | Estabrook et al. ....... 604/164.11 |
| 6,595,960 B2 * | 7/2003 | West et al. .................... 604/181 |

FOREIGN PATENT DOCUMENTS

| WO | WO 00/24440 | 5/2000 |
| WO | WO 00/40282 | 7/2000 |
| WO | WO 01/03754 A2 | 1/2001 |

* cited by examiner

*Primary Examiner* — Nicholas Lucchesi
*Assistant Examiner* — Aarti B Berdichevsky
(74) *Attorney, Agent, or Firm* — Pearne & Gordon LLP

(57) ABSTRACT

The present invention relates to a method and a device for avoiding that any of at least one first or at least one second access device (20, 30) is unintentionally withdrawn from a vessel (11). According to the present invention this is achieved by inserting the first access device in a first direction in the vessel, inserting the second access device in a second direction in the vessel, the second direction being different from the first direction and interconnecting the first and the second access device by providing a fixed length of an interconnecting device (50).

5 Claims, 4 Drawing Sheets

AVOIDING UNINTENTIONAL WITHDRAWAL OF ACCESS DEVICE FROM A VESSEL

FIELD OF THE INVENTION

The present invention relates to a method and a device for avoiding that any of at least one first or at least one second access device is unintentionally withdrawn from a vessel.

BACKGROUND

There are several occasions when access devices, such as needles or catheters or the like, are inserted into a patient. The purpose is often to deliver a liquid to the patient. This liquid may be a saline solution that helps restore the fluid balance of the patient, a glucose solution or other nutritional supplements or a solution containing a drug that should be delivered continuously. It may then be important to make sure that the needles are not unintentionally withdrawn from the patient, especially if this state remains undetected.

Other cases when access devices are regularly inserted into a patient are in blood cleaning treatments such as hemodialysis, hemofiltration, hemodiafiltration or plasmafiltration. For people who have lost all or most of their kidney function, it is necessary to find alternative ways of cleaning the blood. One option is to have a new kidney transplanted. Due to the limited availability of organs, the immunological demands on matching between organ and recipient and a number of other reasons, this possibility is only open to some patients.

One alternative to transplantation is dialysis, which has to be performed at regular intervals, usually several times per week, and takes a few hours each time. In dialysis the waste products in the blood are transported across a membrane to a cleaning fluid. In hemodialysis, the most common form of dialysis, blood is removed from the patients body and pumped into an extracorporeal fluid circuit by means of a blood pump. The extracorporeal fluid circuit includes an external device, a dialyser. The dialyser contains a membrane where blood is flowing on one side and a dialysis fluid is flowing on the other side whereby the blood is purified by means of dialysis. The purified blood is then returned to the body. The blood is usually removed from and returned to the body via access devices in the form of hollow needles, which are preferably inserted into a blood vessel in the lower part of one arm. However also other locations for insertion of the needles are possible. In order to facilitate a frequent access to the blood vessel, and also to increase the available flow of blood in that vessel, it is a common practice to create a so-called arterio-venous fistula. Connecting a suitable artery directly to a vein by a surgical procedure creates the fistula. Another possibility is to surgically insert an artificial vessel, i.e. graft, in between an artery and a vein, which graft is then used for the insertion of the needles. Hereinafter the expression vessel will be used while it is understood that the expression vessel comprises blood vessel as well as artificial vessel, graft, fistula and other types of vessels for use in the herein disclosed technical field.

In either case it is, thus, required to insert access devices into the vessel of the patient, each time a dialysis treatment is to be performed. It is then of utmost importance that the access devices are not unintentionally withdrawn during the treatment. If the arterial access device (the one where blood is removed from the patient) is unintentionally withdrawn without being detected, the blood already in the extracorporeal fluid circuit may continue to be pumped by the blood pump. If the venous access device (the one where the blood is returned to the patient) is still in place the blood will then be returned from the extracorporeal fluid circuit to the patient. When all the blood has been returned to the patient by means of the blood pump and if the blood pump is still in operation, air will be pumped into the patient. This would be potentially harmful to the patient and has to be prevented. If, on the other hand, the venous access device would be unintentionally withdrawn without being noticed, all the blood that should have been returned to the patient will instead be lost to the surrounding area. This may be fatal to the patient already after a few minutes, and should therefore be prevented. If both access devices are withdrawn at the same time, no harmful situation will normally arise, although the blood present in the extracorporeal circuit will be lost. However, if this situation remains undetected for a long time, treatment time is lost.

To prevent unintentional withdrawal of access devices it is normal practice in dialysis machines to measure the pressure in an external tubing, constituting the extracorporeal fluid circuit, upstream of the venous access device. This pressure is usually measured in a drip chamber attached to the dialysis machine. The pressure is measured by means of a pressure sensor. For the detection of unintentional withdrawal of the venous access device from the vessel, any alarm must be connected to tightly limited intervals of acceptable changes of the venous pressure. A problem with this technique is that the pressure at the site of the pressure sensor is a result of static pressures due to a height difference between the drip chamber where the pressure is measured and the tip of the access device where the pressure in the vessel is measured and the pressure drop due to the flow of blood in the external tubing. It may therefore happen that changes in the height difference of the venous access device and the changed flow resistance when the access device is withdrawn counteract each other so that the resulting pressure change is too limited to be detected, i.e. the changes of the venous pressure is kept within the accepted interval. An unintentionally withdrawn venous access device may lead to fatal results for the patient.

There is, thus, a need for devices that may increase the safety against unintentional withdrawal of any access device during dialysis, and a number of methods have been suggested. The suggested methods may be divided in two different classes. One class of methods aims at detecting when any access device is withdrawn in order to give an alarm to the user. The other class of methods aims at physically preventing the withdrawal of any access device.

Detection of withdrawal of any access device may be made e.g. by use of a reed-relay fixed to the skin which can detect the movement of a magnet mounted in the blood tube as suggested in U.S. Pat. No. 5,578,003. Another possibility is to attach fluid sensing devices, e.g. based on measurement of electrical conductivity, on the skin around the access devices, which is suggested in the PCT application WO 99/24145.

These methods do not prevent the withdrawal of access devices, and manual intervention, as a result of the emission of an alarm signal, is therefore needed to avoid a fatal outcome.

Safer in this respect are the devices that aim at preventing the withdrawal of the access devices. Such devices are e.g. disclosed in U.S. Pat. Nos. 3,900,026, 5,084,026, 5,112,313 and 5,449,349. They all describe devices that are attached to the patients skin, either by tape or by straps around the arm, and to which a single access device may be secured. For dialysis two such devices are needed, one for each access device. It is time consuming to secure each access device in this way.

An alternative solution is provided by the device described in U.S. Pat. Nos. 5,911,706, 5,954,691 and 6,013,058 and in PCT applications WO 00/16834, WO 00/16844, WO 00/40282 and WO 00/53245. This device is implanted surgically under the skin, and is brought in permanent connection with the vessel using two access devices, one for extracting blood and one for returning blood, which are also in their entire length located within the patient's body. Each time that a dialysis procedure is to be performed access is gained to the vessel by inserting two access devices in parallel through the skin of the patient and into specially designed ports in the implanted device. These ports are so designed as to close off the access to the vessel when no access devices are inserted. The device is further designed to lock the access devices in their position when they are inserted into the device in order to prevent unintentional withdrawal of the access devices. As a further safety measure, both access devices are linked together so that if one of the access devices would be unintentionally withdrawn despite the locking mechanism, the other access device would also be withdrawn. The device requires a surgical procedure for its insertion. Due to immunological and other mechanisms in the human body, such implanted devices have a very limited lifespan in the body. It is therefore a short-term solution for the blood access to dialysis patients. It is quite a costly device compared to the use of ordinary dialysis access devices.

WO 01/03754 discloses an insertion guide for inserting an arterial access device and a venous access device, respectively, into a vessel in the form of a fistula. The insertion guide guides the respective access device into the fistula. The access devices are secured in their inserted position by means of a latching piece, which is connected to the respective access device and arranged in a recessed channel and locked in position by means of a clamping screw. This device is limited with respect to how, e.g. in respect of choice of directions, access devices may be arranged in the fistula. This device is complicated from the point of view of avoiding unintentional withdrawal of any access device.

DISCLOSURE OF THE INVENTION

One object of the present invention is to provide a method and a device for avoiding that any of at least one first or at least one second access device is unintentionally withdrawn from a vessel. The present invention is provided by securing that the at least one of the first or the at least one of the second access devices is maintained in place by means of the at least one other access device.

According to the present invention this is achieved by inserting the at least one first access device in a first direction in a vessel of the patient, inserting the at least one second access device in a second direction in the vessel, the second direction being different from the first direction and interconnecting the at least one first and the at least one second access device and providing a fixed length of an interconnecting device. As stated above the expression vessel is herein defined so as to comprise blood vessel as well as artificial vessel, graft, fistula and other types of vessels for use in the herein disclosed technical field. What constitutes different first and second directions will be further discussed below. For hemodialysis treatments it is e.g. common practice to let the at least one first or the at least one second access device be directed against the blood stream whereas the other one is facing essentially the opposite direction. It is also common practice to use access devices provided with so-called wings by means of which the access device is secured to the patient by means of tape or the like. In one embodiment of the present invention the at least one first or the at least one second access device is provided with an abutment. The abutment and the wings, respectively, allow insertion of the respective access device a predetermined distance into the vessel before the wing or the abutments prevents the access device to be further inserted. According to the invention the at least one first and the at least one second access device, respectively, is attached and secured to each end of an interconnecting device in such a way that the interconnecting device is placed in between the access devices. This interconnection of the at least one first and the at least one second access device has the effect that if for example the at least one first access device by an external force is pulled in a direction out of the vessel, the force will be transferred by the attached interconnecting device to the at least one second access device. Due to the chosen angle between the first and the second insertion direction of the respective access device this will force the at least one second access device in the direction further into the vessel. However, only very limited movement is possible in this direction, since the access device is stopped both by internal resistance at the tip of the access device and by the external design in the form of a wing or an abutment arranged on the access device as discussed above. The unintentional withdrawal of any of the at least one first or the at least one second access device is thereby avoided.

Sufficiently different first and second insertion directions are herein defined as non-parallel directions. If the first and the second direction is the same, or nearly the same, and the access devices are attached to each other, this will assure that it is impossible to withdraw one access device alone. Instead both access devices will in that case be withdrawn together. This is not satisfactory, since all the blood present in the extracorporeal fluid circuit will then be lost. An angle between the first and the second direction is therefore recommended to be at least in the magnitude of 30° in order to avoid directions, which are nearly the same. Preferably the angle between the first and the second insertion direction is at least in the magnitude of 45° and most preferably in the magnitude of 180°. The expression "in the magnitude of" is herein used in order to take into account that tissue surrounding the area where the respective access devices are inserted is somewhat resilient and that the distance the respective access device is inserted into the vessel may differ.

If the at least one first and the at least one second access device is inserted in a first and a second direction, respectively, where the second direction is substantially opposite to the first direction, the connecting device will prevent any unintentional withdrawal of any of or both of the at least one first and the at least one second access device. A substantially opposite direction comprises insertion directions where the tips of the respective access device are arranged facing each other. In an alternative embodiment the tips are arranged facing away from each other. A further possibility according to the invention is to place the at least one first and the at least one second access device perpendicular to each other. Also other angles are possible according to the invention as long as the withdrawal of the at least one first and/or the at least one second access device would require adjustment, i.e. shortening or elongation (lengthening) of the interconnecting device.

A rod like member may constitute the interconnecting device. The interconnecting device is in one embodiment of the invention designed with a first and a second end each provided with an interlocking device. The interlocking device is optionally arranged on the at least one first and the at least one second access device, respectively. In a further embodiment of the present invention the interlocking device is partly arranged on the interconnecting device and partly on the at least one first and the at least one second access device, respectively, in the form of mating bodies. The interconnecting device is preferably locked onto the respective at least one first and at least one second access device at a position behind any wing or abutment (away from the patient). In order to accommodate the different insertion directions at which the access devices may be inserted, the connection between the interlocking devices at each end of the connecting device and the interconnecting device is preferably made in the form of a ball joint or the like that allows at least partly pivotal connection. This will allow the interlocking device to be positioned in a variety of angles with respect to the interconnecting device.

In an alternative embodiment of the present invention the access devices are designed so that part of the interlocking device is permanently mounted on the access device during production of it. This permanent part of the access device may then include a ball shaped tip, which is designed to fit in a mating holder at the end of the connecting device. The access device is then connected to the interconnecting device by snapping the ball shaped tip into the mating holder of the interconnecting device.

In another embodiment of the present invention the length of the interconnecting device is made adjustable in order to accommodate all possible distances between the access devices that may be desired for different patients or at different occasions. This adjustable length may e.g. be accomplished by a telescopic design of the interconnecting device, whereby two or more parts may be moved more or less into or out of each other. In a further embodiment of the present invention the length of the interconnecting device is made adjustable in a way that two or more parts are movable in relation to each other by sliding the parts over each other or in parallel to each other. When the desired length has been decided, the two or more parts of the interconnecting device are fixed or locked together or in relation to each other by one or more locking mechanisms. The design of the locking mechanism may be such as to allow the interconnecting device to assume any length between its minimum and maximum. The locking mechanism may alternatively be designed to allow the choice of one out of a limited number of lengths.

In one embodiment of the present invention the adjustable length of the interconnecting device in the form of a rod like member is accomplished by splitting the rod like member into two or more separate rod like members that are placed in parallel, but at different positions in the longitudinal direction so as to achieve the desired length.

These separate rod like members are then fixed together at two or more positions. The surface of the rod like members may further be shaped in a saw tooth pattern along one side. Letting the saw tooth patterns of the different rod like members face each other will then prevent any movement of the rod like members in relation to each other after fixation.

Further objects, features and advantages of the present invention will appear from the detailed description of the invention given below with reference to the drawings, which include different embodiments of the invention.

DETAILED DESCRIPTION OF EMBODIMENTS OF THE INVENTION

Figure 1:
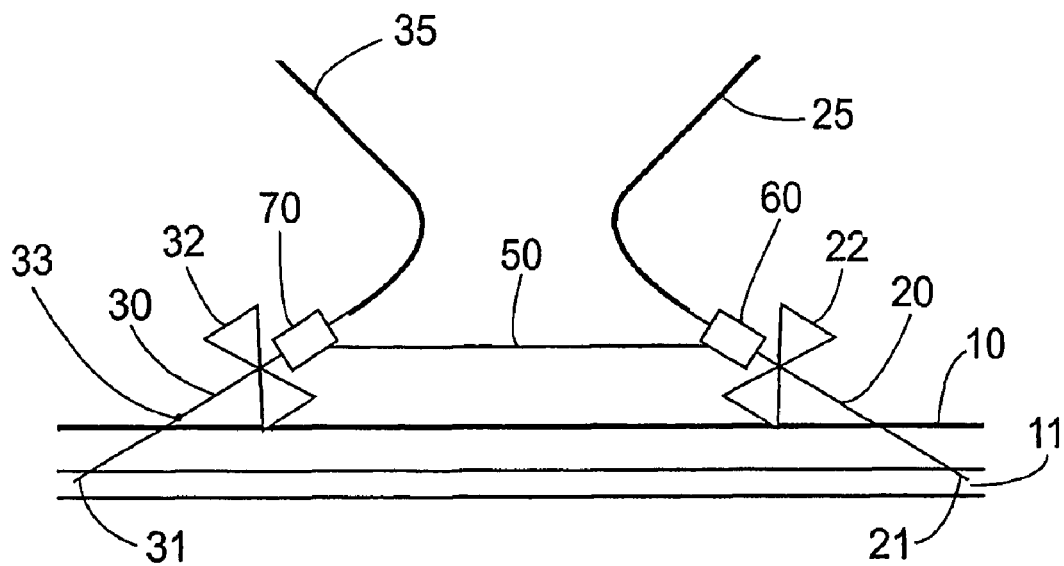
FIG. 1 is a schematic cross-sectional view of a first embodiment of the invention.

One embodiment of the present invention will now be described in detail with reference to the figures. Referring to FIG. 1, a first and a second access device in the form of a first and a second needle 20 and 30 has been inserted through the skin 10 of a patient and into a vessel 11. In the preferred embodiment of the invention the needles are made out of a rigid material, e.g. stainless steel which is often used in medical supplies, and their size may be in the range 14-17 gauge with a length of 20-30 mm as is usually used in hemodialysis. The two needle tips 21 and 31 are facing substantially opposite directions. Each of the needles is provided with a wing 22 and 32. Such wings are often present on such needles. Each end of an interconnecting device in the form of a stiff rod 50 is attached to the respective needle at a position behind the wings 22 and 32, and is secured to the respective needle by means of symbolically shown interlocking devices 60 and 70. Also shown are flexible blood tubes 25 and 35 that lead the blood from the first needle to the not shown extracorporeal fluid circuit, and back again to the second needle.

Figure 2:
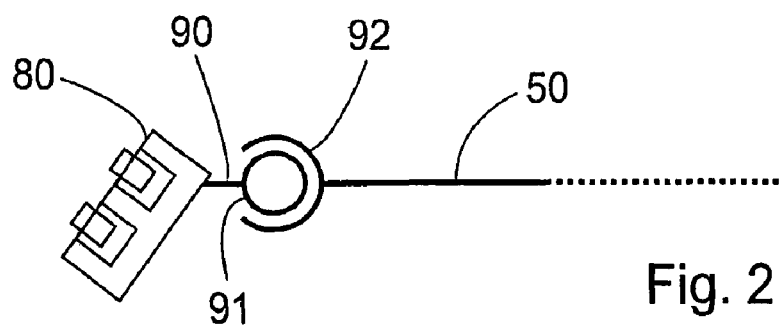
FIG. 2 is a partial view similar to FIG. 1 and shows a symbolic interlocking device.

One embodiment of the symbolically shown interlocking device 70, which corresponds to 60, is shown in FIG. 2. To a needle holder 80 is fixed a connecting rod 90, which ends in a ball 91. Together with a mating ball holder 92 arranged on the interconnecting device the ball 91 forms a ball joint, by which the needle holder 80 is connected to the interconnecting device in the form of the rod 50 in such a way as to allow it to rotate or pivot freely or at least partly freely around the ball 91.

Figure 3:
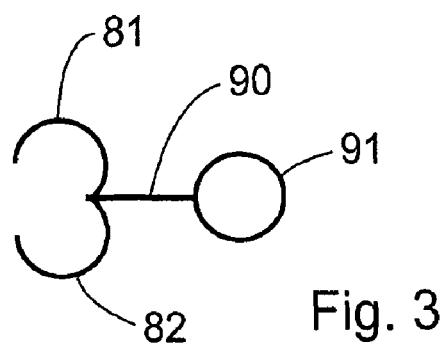
FIG. 3 is a partial plan view of the symbolic interlocking device of FIG. 2.

The symbolically shown interlocking device 70 is shown from above in FIG. 3 with the needle holder 80 in an open position ready to be placed around the needle. The needle holder 80 consists of two halves 81 and 82, each having arms designed to snap around the needle. The arms of half 81 are designed to fit in between the arms of half 82 when the needle holder is closed as indicated in FIG. 2. The arms are further designed in such a way as to allow them to snap together in order to stay in a closed position. The holder 80 is placed on the needle after insertion in the vessel, and may be placed at a suitable location along the needle above the wing 22, 32 and before the tube 25, 35. The needle is optionally provided with a pair of nipples (not shown) in between which the holder 80 is placed and secured from sliding along the needle. In this way, the rod 50, with a fixed length of the rod, may accommodate a certain distance span.

Figure 4:
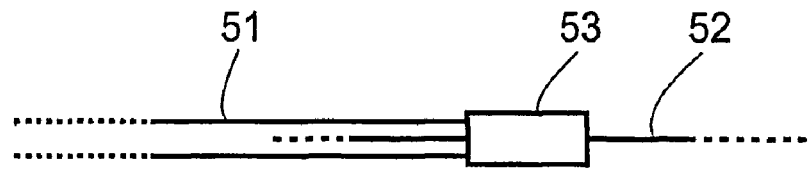
FIG. 4 is a partial plan view of a symbolic telescopic rod interconnecting the access devices of FIG. 1.

In another embodiment of the invention the length of the interconnecting device is adjustable, in steps or continuously. FIG. 4 shows in greater detail, however symbolically, one embodiment of an interconnecting device in the form of a stiff rod 50 with adjustable lengths which is constructed from two rods 51 and 52 as follows. Rod 51 is hollow, with its inner diameter slightly larger than the outer diameter of rod 52. The length of rod 50 is telescopically adjusted by sliding rod 52 into rod 51 until the desired length of rod 50 is achieved. The rods 51 and 52 are secured to each other in this position by tightening a screw 53 on to rod 51. The design of the screw 53 is such that when it is screwed on to rod 51, this will force the end of rod 51 firmly against rod 52 and thus lock it in place. The details of this construction is known per se.

A suggested use of the present invention will now be described. The two access devices in the form of needles to be secured from unintentional withdrawal are first inserted into the vessel of the patient as shown in FIG. 1, with the tips of the needles facing away from each other, and the needles inserted in essentially opposite directions. The screw 53 on the stiff rod 50 in FIG. 4 is opened up so that the two rods 51 and 52 are freely movable to allow the length of stiff rod 50 to be adjusted. One end of the stiff rod 50 is then attached to one of the needles by closing the needle holder halves 81 and 82 around the needle at a position behind the needle wings 22, 32, as shown in FIG. 1 or behind any abutment 33. The two halves 81 and 82 are snapped together so that they will stay in the locked position. The length of the stiff rod is then adjusted, but without tightening the screw 53, so that the other end of the stiff rod 50 can be attached to the second needle. This is done in exactly the same way as for the first needle. When both ends of the interconnecting device have been attached to the respective needle, the needle positions in the vessel of the patient are adjusted if necessary. Finally, the screw 53 is tightened so that the two rods 51 and 52 are fixed to each other, and the length of the stiff rod 50 is fixed and is no longer unintentionally adjustable. To increase the safety even further, the stiff rod 50 may also be taped to the skin of the patient.

The scope of the invention is by no means limited to the embodiment described above.

The access devices may e.g. be placed in other configurations. One alternative is shown in FIG. 5, where the access devices 20 and 30 are still facing essentially opposite directions, but with the tips 21 and 31 facing each other instead of away from each other as in FIG. 1.

Figure 6:
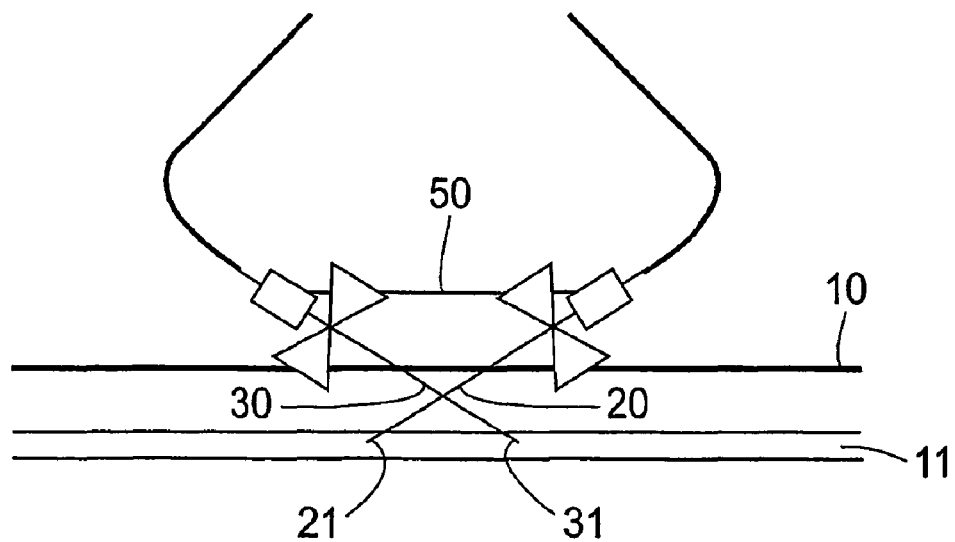
FIG. 6 is a view similar to FIG. 1 with a still different symbolically shown placement of the access devices.

Yet another possible configuration is shown in FIG. 6, where the access devices are crossed.

Figure 5:
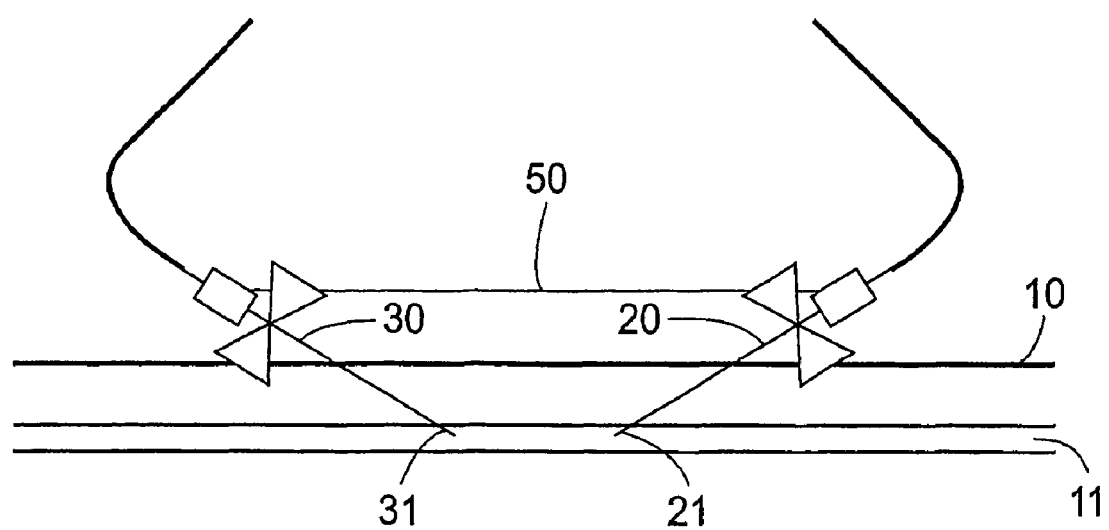
FIG. 5 is a view similar to FIG. 1 with a different symbolically shown placement of the access devices.

As appears from FIGS. 1, 5 and 6, the wings 22,32 are disposed closely to the entrance point through the skin. These wings may be folded down and secured to the skin via tape or the like. Such a wing 22, 32 may optionally be used for limiting the insertion distance of the access device it is related to. If one of the access devices tends to be pulled out due to an external force, the other access device will be pushed further into the skin, until any optional wing 22, 32 or optional abutment 33 abut the skin and prevents further movement of the access device in the insertion direction. Thus, the assembly of the at least one first and the at least one second access device and the interconnecting device may move slightly, but not sufficiently for withdrawing one or more of the access devices. Moreover, frictional forces counteract such movement.

In one embodiment of the present invention the interconnecting device is arranged as close as possible to the skin, since that would prevent unintentional movement. In a further embodiment of the present invention the interconnecting device is attached to the skin with a plaster or strap, in order to further increase safety.

Figure 7:
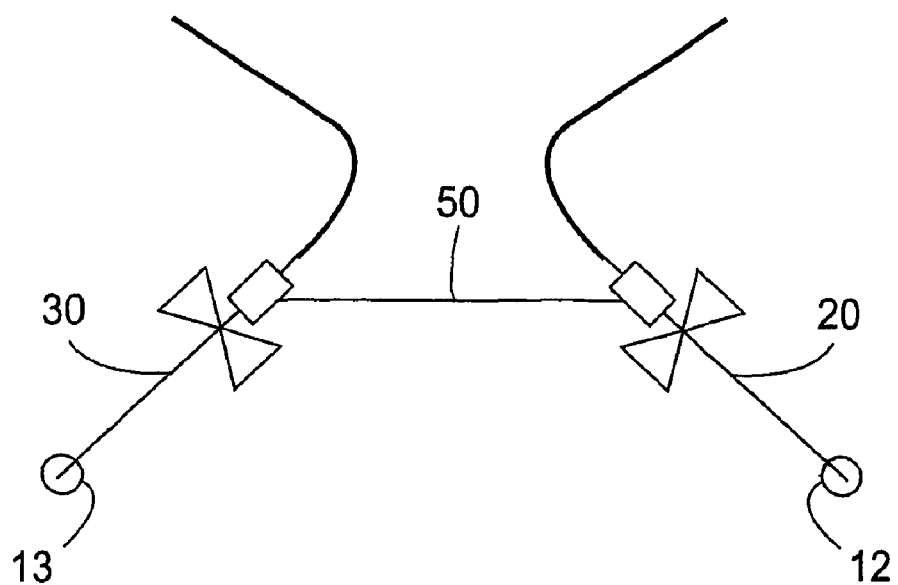
FIG. 7 is a view similar to FIG. 1 with yet another symbolically shown placement of the access devices.

In one embodiment of the present invention the at least one first access device and the at least one second access device are arranged with an angle relative to each other as shown in FIG. 7, where the skin of the patient is shown from above. The access devices here in the form of needles 20 and 30 penetrate the skin through the openings 12 and 13 made by the needles. Provided that the needles are inserted sufficiently deep into the vessel of the patient tissue will prevent the needles from moving sideways, and the interconnecting device 50 will prevent accidental removal of the needles, since this would require adjustment of the length of the interconnecting device 50.

Figure 8:
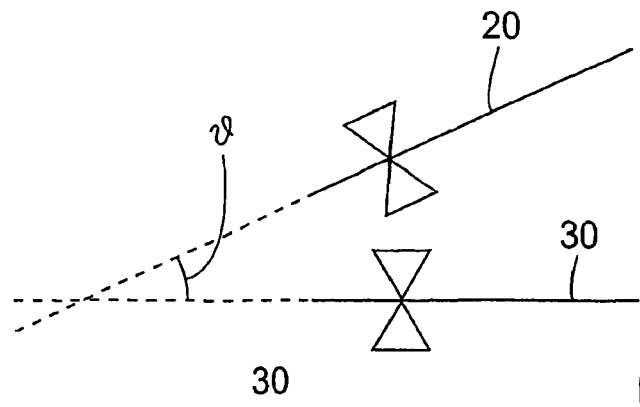
FIG. 8 is a schematic plan view showing the angle between the access devices.

FIG. 8 defines an angle v between the two access devices in the form of needles 20 and 30. Small movements of the interlocking devices 60 and 70 around the needles cannot be ruled out due to production tolerances, the angle v should therefore be greater than zero with some margin. If the needles are produced in a material that is not completely rigid, e.g. a plastic material, this margin needs to be increased. Furthermore, even if the needles are inserted with some depth, i.e. a certain distance into the patient, the tissue may to some extent give away to small sideways movements of the needles. This further increases the demand for a margin against small values of the angle v. It is therefore recommended that v should be in the magnitude of at least 30 degrees, preferably in the magnitude of 45 degrees, most preferably above the magnitude of 90 degrees.

In all of the configurations illustrated in FIG. 1 and in FIGS. 5-8 the access devices in the form of two needles are symmetrically arranged with respect to the surface, such as skin, through which they are inserted. In an alternative embodiment the angles between each of the two needles and the normal to said surface are not equal. In such a case, each needle needs to form an angle with the normal of the surface. Such angle may be in the magnitude of more than 30 degrees and in most cases it is preferred that the angle is in the magnitude of more than 45 degrees, especially when the surface is somewhat flexible, as is the case with the skin.

In all of the configurations illustrated in FIG. 1 and in FIGS. 5-8 the two access devices in the form of needles have further been assumed to reside within a common plane. It is then straightforward to define the angle between the needles as done in FIG. 8. The needles may alternatively be placed in a configuration that does not allow a common plane to be defined wherein both needles are located. The requirement on the needle configuration in such cases is still the same, namely that the withdrawal of one or both of the needles would require adjustment of the length of the connecting rod 50.

Figure 9:
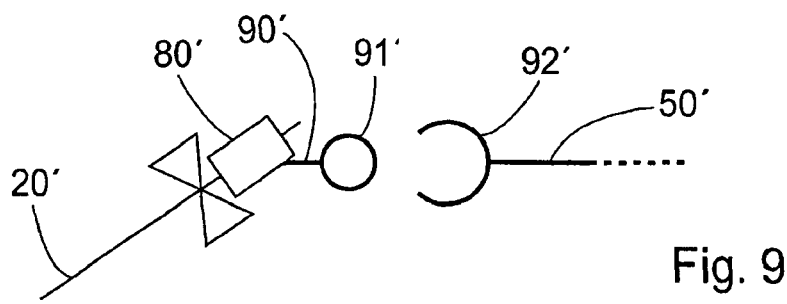
FIG. 9 is a partial view similar to FIG. 2, showing symbolically an alternative interlocking device.

An alternative embodiment of the interlocking device 70 is shown in FIG. 9. When the access device in the form of a needle 20' is produced, the needle holder 80' is permanently attached to the needle as an integral part of it. A connecting rod 90' ending with a ball 91' is permanently attached to the needle holder 80'. The interconnecting device in the form of a stiff rod 50' ends with a ball holder 92' designed to mate with the ball 91'. The stiff rod 50' is connected to the needle 20' by snapping the ball 91' into the ball holder 92' so that a ball joint is formed.

In an alternative embodiment, not specifically shown but corresponding to FIG. 9, the access device in the form of a needle 20' is produced in such a way that it is provided with a ball holder 92'. The interconnecting device in the form of a stiff rod 50' is provided with a ball 91' permanently attached to its end. The ball holder 92' is designed to mate with the ball 91'. The needle 20' is connected to the stiff rod 50' by snapping the ball 91' into the ball holder 92' so that a ball joint is formed.

Figure 10:
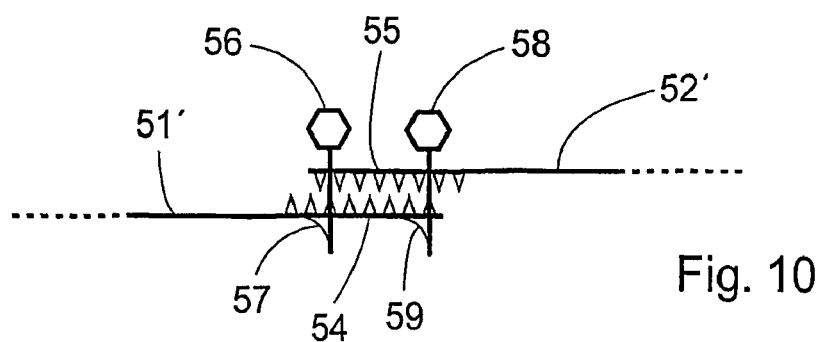
FIG. 10 is a plan view of a symbolically shown rod locking mechanism.

FIG. 10 shows schematically an alternative way of making the length of the interconnecting device in the form of a stiff rod 50 adjustable by constructing it as two rods 51' and 52' each having a saw tooth pattern along one side. The two rods 51' and 52' are moved along each other, but at some distance from each other so that the saw tooth patterns 54 and 55 do not interact, until the correct length has been achieved. By moving the two rods together, the saw tooth patterns will mate, and the length is fixed. The two rods are optionally kept in place by two pins 56 and 58 that are inserted from above through both rods 51' and 52' through mating holes in both rods. The lower ends of pins 56 and 58 have hooks 57 and 59 that fold out when they pass out of the holes in rod 51' and which make sure that the pins cannot be retracted again.

In an alternative embodiment of the present invention the interconnection device includes a Velcro® fastening in a fashion similar to what is shown in FIG. 10 but for the locking pins 56, 58.

Figure 11:
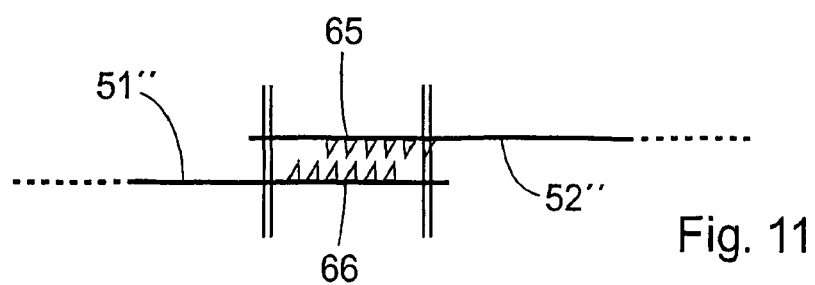
FIG. 11 is a plan view of a symbolically shown different rod locking mechanism.

In the case of FIG. 1, the interconnecting device in the form of a rod 50 may not shorten or decrease its length after application and fixation. In an alternative embodiment the rod may be arranged to be elongated or lengthened but be prevented from being shortened. The first access device in the form of a needle is inserted. Then the second access device also in the form of a needle is inserted, and at the same time, the rod is elongated during the insertion. When the insertion is finalized, the rod has been elongated as required. The mechanism is so arranged that the rod cannot be unintentionally shortened again. Thus, a very convenient double needle assembly is obtained. The arrangement may be of a conventional nature, for example including two rods 51" and 52" having teeth 65 and 66 permitting elongation but preventing shortening, as shown schematically in FIG. 11.

In the embodiment of FIG. 5, the opposite action should occur, namely that the interconnecting device in the form of a rod may not be unintentionally lengthened after insertion of the access devices in the form of a pair of needles.

The interconnecting device may be manufactured in plastic material being sufficiently rigid for the intended operation, such as an acrylic material or PVC, which is often used for medical purposes.

As already indicated above there may be more than one first and/or more than one second access devices that are interconnected according to the invention. Thus, there may be arranged a hub, to which several first and second access devices may be attached to form an aggregate of first and second access devices. At least one first and at least one second access device need to be arranged according to the present invention.

The invention is intended to cover any pair of access devices passing through a surface that may be interconnected according to the invention. Thus, also catheters that are flexible may be interconnected by means of the interconnecting device, provided that they are inserted deeply into the vessel so that they cannot flex out of the holes 12, 13.

The invention has been described in connection with access devices for hemodialysis or similar treatment. However, every access situation where two access sites are required may benefit from the present invention. Thus, in the provision of nutritional solution or medicaments, in which situation only a single access device normally is used, two access devices are sometimes required in case one of the access device may be occluded.

The invention claimed is:

1. Method of avoiding unintentional withdrawal of any of at least one first or at least one second access device (20, 20', 30) from a vessel (11), which comprises;
inserting the at least one first access device in a first direction in the vessel;
inserting the at least one second access device in a second direction in the vessel, the second direction being different from the first direction; and
interconnecting the at least one first and the at least one second access device by providing a fixed length of an interconnecting device (50, 50', 51', 51", 52', 52") comprising
fixing the interconnecting device between the at least one first access device and the at least one second access device,
characterized in adjusting the length of the interconnecting device (50, 50', 51', 51", 52', 52") before intentionally withdrawing the at least one first or the at least one second access device (20, 20', 30).

2. Method of avoiding unintentional withdrawal of any of at least one first or at least one second access device (20, 20', 30) from a vessel (11), which comprises;
inserting the at least one first access device in a first direction in the vessel;
inserting the at least one second access device in a second direction in the vessel, the second direction being different from the first direction; and
interconnecting the at least one first and the at least one second access device by providing a fixed length of an interconnecting device (50, 50', 51', 51", 52', 52") comprising
fixing the interconnecting device between the at least one first access device and
the at least one second access device, characterized in inserting the at least one first or the at least one second access device (20, 20', 30) a predetermined distance into the vessel (11), and characterized in interconnecting the at least one first and the at least one second access device by the interconnecting device (50, 50', 51', 51", 52', 52") before inserting.

3. Device which comprises at least one first and at least one second access device (20, 20', 30), the at least one first access device to be inserted in a vessel pointing in a first direction and the at least one second access device to be inserted in the vessel pointing in a second direction, the second direction being different from the first direction, characterized in that the at least one first and the at least one second access device are reconnected by means of an interconnecting device (50, 50', 51', 51", 52', 52") having a length to be fixed between the at least one first and the at least one second access device such that that unintentional withdrawal from the vessel of any of the at least one first or the at least one second access device is avoided, characterized in that a rod that is of adjustable length constitutes the interconnecting device (50, 50', 51', 51", 52', 52").

4. Device which comprises at least one first and at least one second access device (20, 20', 30), the at least one first access device to be inserted in a vessel pointing in a first direction and the at least one second access device to be inserted in the vessel pointing in a second direction, the second direction being different from the first direction, characterized in that the at least one first and the at least one second access device are reconnected by means of an interconnecting device (50, 50', 51', 51", 52', 52") having a length to be fixed between the at least one first and the at least one second access device such that that unintentional withdrawal from the vessel of any of the at least one first or the at least one second access device is avoided, characterized in that the interconnecting device (50, 51', 51", 52', 52") is attached to the at least one first and the at least one second access device (20, 20', 30), respectively, via an interlocking device (60, 70, 80, 80', 81, 82, 90, 90', 91, 91', 92, 92'), further characterized in that the interlocking device comprises a ball (91') integrated with any of the at least one first or the at least one second access device (20, 20', 30) and a ball holder (92') integrated with the interconnecting device (50, 50', 51', 51", 52', 52").

5. Device which comprises at least one first and at least one second access device (20, 20', 30), the at least one first access device to be inserted in a vessel pointing in a first direction and the at least one second access device to be inserted in the vessel pointing in a second direction, the second direction being different from the first direction, characterized in that the at least one first and the at least one second access device are reconnected by means of an interconnecting device (50, 50', 51', 51", 52', 52") having a length to be fixed between the at least one first and the at least one second access device such that that unintentional withdrawal from the vessel of any of the at least one first or the at least one second access device is avoided, characterized in that the interconnecting device (50, 51', 51", 52', 52") is attached to the at least one first and the at least one second access device (20, 20', 30), respectively, via an interlocking device (60, 70, 80, 80', 81, 82, 90, 90', 91, 91', 92, 92'), further characterized in that the interlocking device comprises a ball (91') integrated with the interconnecting device (50, 50', 51', 51", 52', 52") and a ball holder (92') integrated with any of the at least one first or the at least one second access device (20, 20', 30).

\* \* \* \* \*